United States Patent [19]

Hoshino et al.

[11] Patent Number: 5,478,822
[45] Date of Patent: Dec. 26, 1995

[54] TETRAHYDROBENZAZEPINE DERIVATIVES WHICH INHIBIT LIPOXYGENASE

[75] Inventors: Yoko Hoshino, Nishio; Takafumi Ikeda, Handa, both of Japan

[73] Assignee: Pfizer Inc., New York, N.Y.

[21] Appl. No.: 167,959

[22] PCT Filed: May 27, 1992

[86] PCT No.: PCT/US92/04197

§ 371 Date: Dec. 17, 1993

§ 102(e) Date: Dec. 17, 1993

[30] Foreign Application Priority Data

Jun. 28, 1991 [JP] Japan ..................... 3-158832

[51] Int. Cl.$^6$ ............... C07D 223/16; A61K 31/55
[52] U.S. Cl. ........................... 514/213; 540/593
[58] Field of Search .................... 540/593; 514/213

[56] References Cited

U.S. PATENT DOCUMENTS 4,981,865  1/1991  Belliotti et al. ................ 514/480

FOREIGN PATENT DOCUMENTS 196184  10/1986  European Pat. Off. .
279263   8/1988  European Pat. Off. .
292699  11/1988  European Pat. Off. .

OTHER PUBLICATIONS

J. March, Advanced Organic Chemistry, 1992, pp. 448, 771, 958–959.

*Primary Examiner*—Emily Bernhardt

*Attorney, Agent, or Firm*—Peter C. Richardson; Paul H. Ginsburg; Bryan C. Zielinski

[57] ABSTRACT

Compounds of the formula

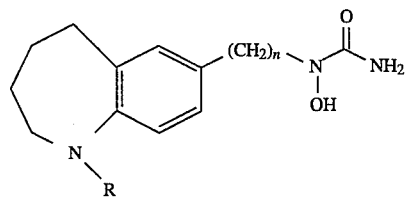

wherein n is 1 to 5 and R is hydrogen, $C_1$ to $C_4$ alkyl, arylalkyl having from one to four carbon atoms in the alkyl moiety or arylalkyl substituted with one or more substituents selected independently from the group consisting of halogen, nitro, cyano, $C_1$ to $C_6$ alkyl, $C_1$ to $C_6$ alkoxy, $C_1$ to $C_6$ halosubstituted alkyl, $C_1$ to $C_6$ hydroxysubstituted alkyl, $C_2$ to $C_7$ alkoxycarbonyl and aminocarbonyl, and the pharmaceutically acceptable salts thereof, inhibit the enzyme lipoxygenase and are useful in treating allergy and inflammatory and cardiovascular conditions for which the action of lipoxygenase has been implicated. These compounds form the active ingredient in pharmaceutical compositions for treating such conditions.

14 Claims, No Drawings

TETRAHYDROBENZAZEPINE DERIVATIVES WHICH INHIBIT LIPOXYGENASE

This application is a 371 of PCT/US 92/04197 filed May 27, 1992.

BACKGROUND OF THE INVENTION

Field of the Invention

This invention relates to novel tetrahydrobenzazepine N-hydroxyurea derivatives. The compounds of the present invention inhibit the action of the enzyme lipoxygenase and are useful in the treatment or alleviation of inflammatory diseases, allergy and cardiovascular diseases in mammals. This invention also relates to pharmaceutical compositions comprising such compounds and to the use of such compounds in treating inflammatory diseases, allergy and cardiovascular diseases in mammals. This invention further relates to methods of making such compounds.

Arachidonic acid is known to be the biological precursor of several groups of endogenous metabolites, prostaglandins including prostacyclins, thromboxanes and leukotrienes. The first step of arachidonic acid metabolism is the release of arachidonic acid and related unsaturated fatty acids from membrane phospholipids, via the action of phospholipase. Free fatty acids are then metabolized either by cyclooxygenase to produce the prostaglandins and thromboxanes or by lipoxygenase to generate hydroperoxy fatty acids which may be further converted to the leukotrienes. Leukotrienes have been implicated in the pathophysiology of inflammatory diseases, including rheumatoid arthritis, gout, asthma, ischemia reperfusion injury, psoriasis and inflammatory bowel disease. Any drug that inhibits lipoxygenase is expected to provide significant new therapy for both acute and chronic inflammatory conditions.

Several review articles on lipoxygenase inhibitors have been reported (See H. Masamune et al., *Ann. Rep, Med. Chem.*, 24, 71–80 (1989) and B. J. Fitzsimmons et al., *Leukotrienes and Lipoxygenases*, 427–502 (1989).

Compounds of the same general class as the compounds of the present invention are disclosed in EP 279263 A2, EP 196184 A2, JP (Kohyo) 502179/88 and U.S. Pat. No. 4,822,809.

SUMMARY OF THE INVENTION

The present invention provides novel tetrahydrobenzazepine N-hydroxyurea derivatives of the following formula and their pharmaceutically acceptable salts:

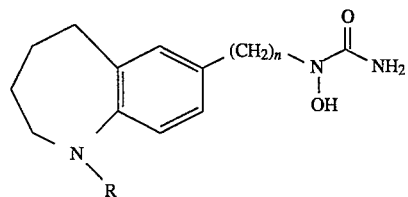

(I)

wherein n is 1 to 5; R is hydrogen, $C_1$ to $C_4$ alkyl, arylalkyl having from one to four carbon atoms in the alkyl moiety or arylalkyl substituted with one or more substituents selected independently from the group consisting of halogen, nitro, cyano, $C_1$ to $C_6$ alkyl, $C_1$ to $C_6$ alkoxy, $C_1$ to $C_6$ halosubstituted alkyl, $C_1$ to $C_6$ hydroxysubstituted alkyl, $C_2$ to $C_7$ alkoxycarbonyl and aminocarbonyl.

This invention also concerns pharmaceutical compositions comprising a pharmaceutically acceptable carder or diluent and a compound of the invention or a pharmaceutically acceptable salt thereof. This invention further concerns methods of treating inflammatory diseases, allergy and cardiovascular diseases in mammals comprising administration of such compounds or compositions.

DETAILED DESCRIPTION OF THE INVENTION

Definitions

As used herein, the following definitions are used.

"Halo" and "halogen" mean radicals derived from the elements fluorine, chlorine, bromine and iodine.

"Alkyl" means straight or branched saturated hydrocarbon radicals, for example, methyl, ethyl, n-propyl and isopropyl.

"Alkoxy" means —$OR^1$ wherein $R^1$ is an alkyl radical, for example, methoxy, ethoxy, propoxy, isopropoxy and butoxy.

"Alkoxycarbonyl" means —$C(=O)R^2$ wherein $R^2$ is an alkoxy radical, for example, methoxycarbonyl, ethoxycarbonyl and propoxycarbonyl.

"Arylalkyl" means an aromatic radical appended to an alkyl radical, for example, phenylethyl(benzyl), phenylethyl, phenylpropyl, phenylbutyl and naphthylmethyl.

"Hydroxysubstituted alkyl" refers to an alkyl radical as described above substituted with one or more hydroxy radicals, for example, hydroxymethyl, dihydroxyethyl and trihydroxypropyl.

Some of the compounds of the above formula may form acid salts. The pharmaceutically acceptable acid salts are those formed from acids which form non-toxic acid salts, for example, hydrochloride, hydrobromide, sulfate or bisulfate, phosphate or acid phosphate, acetate, citrate, fumarate, gluconate, lactate, maleate, succinate, tartrate, methansulfonate, benzensulfonate, toluene-sulfonate, and formate salts.

This invention includes pharmaceutical compositions for treatment of inflammatory diseases, allergy and cardiovascular diseases in a mammal which comprises a pharmaceutically acceptable carder or diluent and a compound of the above formula or a pharmaceutically acceptable salt thereof.

This invention also includes pharmaceutical compositions for inhibiting the lipoxgenase in a mammal which comprises a pharmaceutically acceptable carrier and a compound of the above formula or a pharmaceutically acceptable salt thereof.

The novel compounds of this invention may be prepared as shown in the reaction scheme described below.

GENERAL SYNTHETIC SCHEME

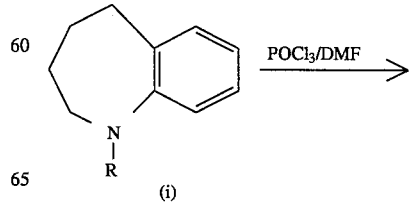

-continued
GENERAL SYNTHETIC SCHEME

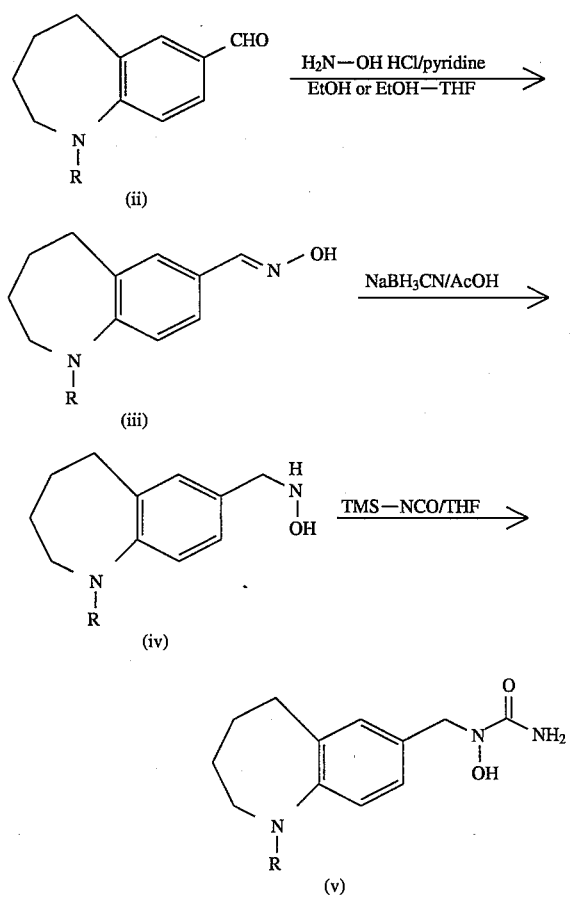

The compounds of the invention may be prepared by a number of synthetic methods. Except where otherwise indicated, in the above reaction scheme and discussion that follow, R and n are as previously defined.

In one embodiment, the compounds of the invention (v) are prepared according to the reaction steps explained in detail as follows.

The starting materials used in the procedure of the above reaction scheme may be prepared from commercially available compounds or known compounds according to standard methods known in the art.

In the first step, aldehyde derivatives (ii) are easily prepared from the corresponding benzazepine derivatives (i) by standard methods known in the art (Vilsmeier reaction).

Generally, the reaction is run for several minutes to several hours. The reaction temperature may range from room temperature to about 100° C. Suitable N-disubstituted formamide agents are selected from N,N-dimethylformamide (DMF) and N-methyl-N-formanilide (MFA). Suitable chloride agents are selected from phosphorus oxychloride (POCl$_2$) and thionyl chloride (SOCl$_2$). If necessary, dichloromethane can be utilized as a reaction-inert solvent. The product can be isolated and purified by conventional procedures, such as recrystallization or chromatography.

In the second step, the aldehyde (ii) is treated with hydroxylamine hydrochloride to afford the oxime (iii). This reaction is carded out in a reaction-inert solvent in the presence of suitable base such as pyridine or triethylamine usually at room temperature. Suitable solvents which do not react with reactants and/or products include, for example, ethanol, THF and mixtures thereof. The oxime (iii) thus obtained is isolated by standard methods. Without further purification, in the next step, the oxime (iii) is converted to the requisite hydroxylamine (iv) with a suitable reducing agent (for example, see R. F. Borch et al, *J. Am. Chem. Soc.*, 93, 2897 (1971)). Reducing agents of choice include, but are not limited to, sodium cyanoborohydride and borane-complexes such as boron-pyridine, boron-triethylamine and boron-dimethylsulfide, however, triethylsilane in trifluoroacetic acid may also be employed.

The aforementioned hydroxylamine (iv) is easily prepared by standard synthetic procedures from readily available carbonyl compounds, i.e, ketone, aldehyde, alcohol or halogen compounds (for example, see R. L. Danheiser et al., *Tetrahedron Lett.*, 28, 3299 (1987), M. Kolobieiski et al., *J. Am. Chem. Soc.*, 79, 5820 (1957), Y. Kobayashi et al., *J. Org. Chem.*, 47, 3232 (1982) and Fieser et al., *J. Am. Chem. Soc.*, 70, 3147 (1948)).

Alternatively the hydroxylamine (iv) can be prepared by treating the corresponding alcohol with N,O-bis(tert-butyloxycarbonyl)hydroxylamine under Mitsunobu-type reaction conditions followed by acid catalyzed hydrolysis of the N,O-protected intermediate product (see JP(Kokai) 45344/89).

The aforementioned hydroxylamine (iv) may also be prepared from a suitable halide compound by reaction with O-protected hydroxylamine and subsequent deprotection (see W. P. Jackson et al., *J. Med. Chem.*, 31, 499 (1988)). Preferred O-protected hydroxylamines include, but are not limited to, O-tetrahydropyranyl-, O-trimethylsilyl- and O-benzylhydroxylamine.

The hydroxylamine of formula (iv) thus obtained by the abovementioned representative procedures is isolated by standard methods and purification can be achieved by conventional means, such as recrystallization and chromatography.

In the last step, the hydroxylamine (iv) is treated with trimethylsilylisocyanate (TMS-NCO) in a reaction-inert solvent usually at ambient through to reflux temperature. Suitable solvents which do not react with reactants and/or products include, for example, tetrahydrofran, dioxane, methylene chloride and benzene. An alternative procedure employs treatment of the hydroxylamine (iv) with gaseous hydrogen chloride in a reaction-inert solvent such as benzene or toluene and then subsequent treatment with phosgene, Reaction temperatures are usually in the range of ambient temperature through to boiling point of solvent. The intermediate carbamoyl chloride is not isolated but subjected to (i.e. in situ) reaction with aqueous ammonia. The urea compound (v) thus obtained is isolated by conventional means, such as recrystallization and chromatography.

The pharmaceutically acceptable salts of the novel compounds of the present invention are readily prepared by contacting said compounds with a stoichiometric amount of, in the case of a non-toxic cation, an appropriate metal hydroxide or alkoxide or amine in either aqueous solution or a suitable organic solvent, or, in the case of a non-toxic acid salt, an appropriate mineral or organic acid in either aqueous solution or a suitable organic solvent. The salt may then be obtained by precipitation or by evaporation of the solvent.

The compounds of this invention inhibit the activity of the enzyme lipoxygenase. This inhibition has been demonstrated by an assay using rat peritoneal cavity-resident cells which determines the effect of said compounds on the metabolism of arachidonic acid.

All of the compounds of Examples 1 to 4 were tested according to the methods described in "Synthesis of leukotrienes by peritoneal macrophages," *Jap. J. Inflammation,* 7, 145–150 (1987), and were shown to be lipoxygenase inhibitors, exhibiting $IC_{50}$ values in the range of about 0.199 to about 3.16 µM, for lipoxygenase inhibition.

The ability of the compounds of the present invention to inhibit lipoxygenase makes them useful for controlling the symptoms induced by the endogenous metabolites arising from arachidonic acid in a mammalian subject. The compounds are therefore valuable in the prevention and treatment of such disease states in which the accumulation of arachidonic acid metabolites are the causative factor, e.g., allergic bronchial asthma, skin disorders, rheumatoid arthritis, osteoarthritis and thrombosis.

The compounds of formula (I) and their pharmaceutically acceptable salts are of particular use in the treatment or alleviation of inflammatory diseases, allergy and cardiovascular diseases in a human subject as well in the inhibition of lipoxygenase.

Methods of Administration

For treatment of the various conditions described above, the compounds of the invention and their pharmaceutically acceptable salts can be administered to a human subject either alone or, preferably, in combination with pharmaceutically acceptable carders or diluents in a pharmaceutical composition, according to standard pharmaceutical practice. A compound can be administered via a variety of conventional routes of administration including orally, parenterally and by inhalation. When the compounds are administered orally, the dose range will generally be from about 0.1 to about 20 mg/kg/day, based on the body weight of the subject to be treated, preferably from about 0.1 to about 1.0 mg/kg/day in single or divided doses. If parenteral administration is desired, then an effective dose will generally be from about 0.1 to about 1.0 mg/kg/day. In some instances it may be necessary to use dosages outside these limits, since the dosage will necessarily vary according to the age, weight and response of the individual patient as well as the severity of the patient's symptoms and the potency of the particular compound being administered.

For oral administration, the compounds of the invention and their pharmaceutically acceptable salts can be administered, for example, in the form of tablets, powders, lozenges, syrups or capsules, or as an aqueous solution or suspension. In the case of tablets for oral use, carriers which are commonly used include lactose and corn starch. Lubricating agents such as magnesium stearate are commonly added. In the case of capsules, useful diluents are lactose and dried corn starch. When aqueous suspensions are required for oral use, the active ingredient is combined with emulsifying and suspending agents. If desired, certain sweetening and/or flavoring agents can be added.

For intramuscular, intraperitoneal, subcutaneous and intravenous use, a sterile solution of the active ingredient is usually prepared, and the pH of the solutions should be suitably adjusted and buffered. For intravenous use, the total concentration of solute should be controlled to make the preparation isotonic.

EXAMPLES

The present invention is illustrated by the following examples. However, it should be understood that the invention is not limited to the specific details of these examples.

Proton nuclear magnetic resonance spectra (NMR) were measured at 270 MHz unless otherwise indicated and peak positions are expressed in parts per million (ppm) downfield from tetramethylsilane. The peak shapes are denoted as follows: s, singlet; d, doublet; t, triplet; q, quartet; m, multiplet; br, broad.

Example 1 N-Hydroxy-N-(1-benzyl-2,3,4,5-tetrahydro-1H-1-benzazepin-7-yl)methylurea

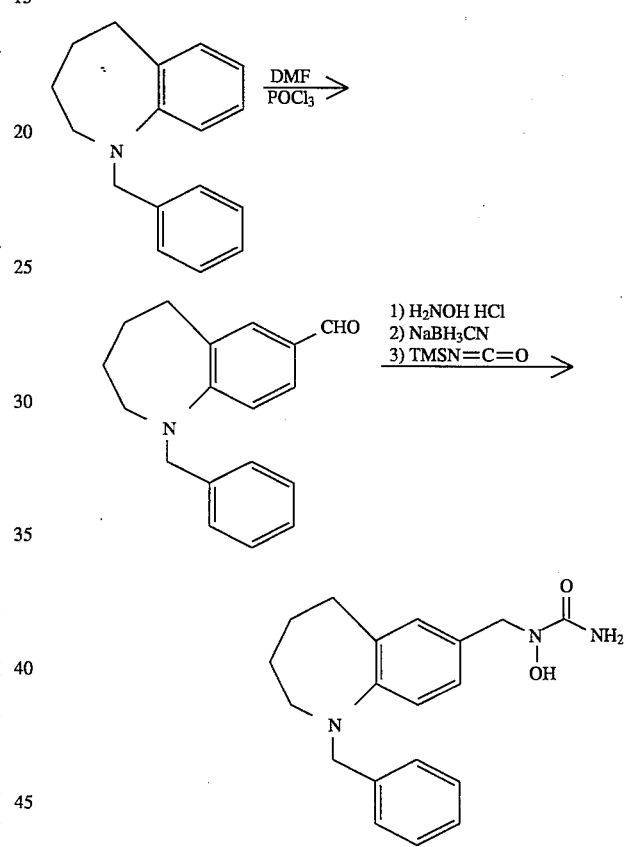

Step 1,
1-Benzyl-1H-1-benzazepin-7-carboxaldehyde

Phosphorus oxychloride (1.9 ml, 20.4 retool) was added to DMF (10 ml) at ambient temperature and the mixture was stirred for 30 minutes under nitrogen atmosphere. To the mixture was added crude 1-benzyl-1H-1-benzazepine (3.23 g, 13.6 mmol) in DMF (5 ml) at ambient temperature. The mixture was stirred at ambient temperature for 1 hour and at 70° C. for 2 hours. Water (35 ml) was added and the mixture was stirred for 10 minutes. The mixture was extracted with EtOAc (2×100 ml) and the combined extracts were washed with $H_2O$ (2×50 ml), saturated $NaHCO_3$ solution (50 ml) and brine (50 ml). The solution was dried over $MgSO_4$ and concentrated in vacuo affording the title compound as a brown oil (3.42 g).

$^1$H NMR (270 MHz, $CDCl_3$) δ 9.77 (s, 1H), 7.63-7.50 (m, 2H), 7.40-7.20 (m, H), 6.85 (d, J=7.9 Hz, 1H), 4.48 (s, 2H), 3.30-3.20 (m, 2H), 3.00-2.90 (m, 2H), 1.89-1.63 (m, 4H).

Step 2, N-Hydroxy-N-(1-benzyl-2,3,4,5-tetrahydro-1H-1-benzazepin-7-yl)-methylurea To a solution of 1-benzyl-1H-1-benzazepin-7-carboxaldehyde (3.42 g, 12.9 mmol) in pyridine (6.5 ml) and EtOH (6.5 ml) was added $H_2N$-OH.HCl (1.34 g, 19.3 mmol) and the mixture was stirred at ambient temperature for 1 hour, concentrated in vacuo and extracted with EtOAc (100 ml) and $H_2O$ (80 ml). The aqueous layer was extracted with EtOAc (30 ml). The combined extracts were washed with $H_2O$ (2×50 ml) and brine (30 ml). The solution was dried over $MgSO_4$ and concentrated in vacuo to give a brown oil (3.60 g). Without purification, the oxime (3.60 g, 12.8 mmol) was dissolved in AcOH (12 ml) and $NaBH_3CN$ (1.02 g, 16.2 mmol) was added portionwise over a period of 45 minutes and the mixture was stirred for 1 hour. To the mixture was added dropwise 10N NaOH (10 ml) under ice bath and the mixture was brought to pH 9 with the addition of $Na_2CO_3$. The mixture was extracted with EtOAc (2×30 ml) and the combined extracts were washed with $H_2O$ (2×50 ml) and brine (50 ml). The solution was dried over $MgSO_4$ and concentrated in vacuo to afford the corresponding hydroxylamine as yellow oil (3.31 g, 92% yield). Without purification, the product was dissolved in THF (12 ml) and to the solution was added 90% TMSN=C=O (2.4 ml, 17.6 mmol) and the mixture was stirred at ambient temperature overnight. Water (2 ml) was added to the mixture, which was then stirred for 10 minutes. The mixture was concentrated in vacuo affording a yellow oil (4.2 g). Chromatography on silica gel (100 g) eluted with $CH_2Cl_2$:EtOH:EtOAc (30:1:1) afforded a colorless oil (3.01 g). Crystallization from EtOAc afforded the title compound as a white solid (1.06 g, 24% overall yield), m.p. 81.6°–83.4° C. (dec.).

IR ν (KBr): 3450, 3200, 2920, 1650.

NMR δ (DMSO): 9.25 (s, 1H), 7.41 (d, J=7.5 Hz, 2H), 7.33 (t, J=7.5 Hz, 2H), 7.23 (t, J=7.5 Hz, 1H), 7.04-6.96 (m, 2H), 6.91 (d, J=8.1 Hz, 1H), 6.25 (s, 2H), 4.39 (s, 2H), 4.29 (s, 2H), 2.88-2.73 (m, 4H), 1.64-1.46 (m, 4H).

Example 2 N-Hydroxy-N-[1-(3-methoxybenzyl)-2,3,4,5-tetrahydro-1H-1-benzazepin-7-yl]methylurea

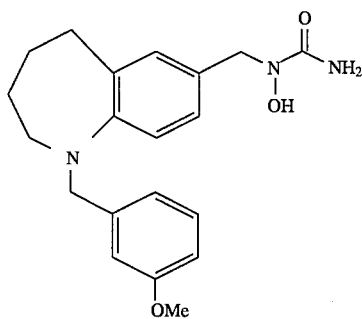

The title compound, m.p. 38°–42° C., was synthesized according to the procedure of Example 1 from 1-(3-methoxybenzyl)-1H-1-benzazepine.

IR ν (KBr): 3500, 3400, 1740, 1650.

NMR δ (DMSO): 9.24 (s, 1H), 7.24 (t, J=8.1 Hz, 1H), 7.04-6.94 (m, 4H), 6.89 (d, J=8.1 Hz, 1H), 6.79 (dd, J=8.1 -2.2 Hz, 1H), 6.27 (s, 2H), 4.39 (s, 2H), 4.26 (s, 2 H), 3.73 (s, 3H), 2.86-2.74 (m, 4H), 1.65-1.46 (m, 4H).

Example 3 N-Hydroxy-N-(1-ethyl-2,3,4,5-tetrahydro-1H-1-benzazepin-7-yl)methylurea

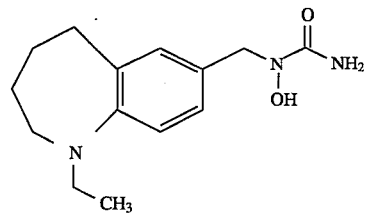

The title compound was synthesized according to the procedure of Example 1 from 1-ethyl-1H-1-benzazepine.

IR ν (CHCl₃): 2930, 1680, 1565, 1505.

NMR δ (DMSO): 9.23 (s, 1H), 7.03-6.96 (m, 2H), 6.82 (d, J=7.7 Hz, 1H), 6.26 (s, 2H), 4.39 (s, 2H), 3.10 (q, J=7.7 Hz, 2H), 2.87-2.79 (m, 2H), 2.71-2.62 (m, 2H), 1.70-1.58 (m, 2H), 1.58-1.45 (m, 2H), 1.11 (t, J=7.7 Hz, 3H).

Example 4 N-Hydroxy-N-[3-(1-ethyl-2,3,4,5-tetrahydro-1H-1-benzazepin-7-yl)propyl]urea

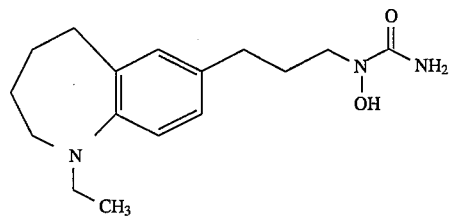

The title compound was synthesized according to the procedure of Example 1 from 1,7-diethyl-1H-1-benzazepine.

IR ν (CHCl₃): 2930, 1655, 1570, 1505.

NMR δ (DMSO): 9.22 (s, 1H), 6.96-6.87 (m, 2H), 6.79 (d, J=8.4 Hz, 1H), 6.24 (s, 2H), 3.46-3.25* (2H), 3.07 (q, J=7.0 Hz, 2H), 2.85-2.77 (m, 2H), 2.69 -2.61 (m, 2H), 2.45 (t, J=7.7 Hz, 2H), 1.73 (t, J=7.1 Hz, 2H), 1.69-1.58 (m, 2H), 1.56-1.44 (m, 2H), 1.10 (t, J=7.0 Hz, 3H).

*This peak was hidden by $H_2O$ in DMSO-$d_6$.

We claim:
1. A compound of the formula

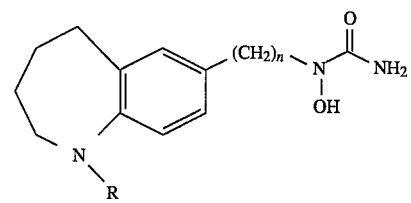

or a pharmaceutically acceptable salt thereof, wherein:

n is 1;

R is hydrogen, $C_1$ to $C_4$ alkyl, or arylalkyl, wherein in said arylalkyl the aryl moiety is a phenyl or naphthyl group and the alkyl moiety has from one to four carbon atoms, and wherein said arylalkyl is optionally substituted by one or more substituents selected independently from the group consisting of halogen, nitro, cyano, $C_1$ to $C_6$ alkyl, $C_1$ to $C_6$ alkoxy, $C_1$ to $C_6$ halosubstituted alkyl, $C_1$ to $C_6$ hydroxysubstituted alkyl, $C_2$ to $C_7$ alkoxycarbonyl and aminocarbonyl.

2. A compound according to claim 1 wherein R is $C_1$ to $C_4$ alkyl.

3. A compound according to claim 1 wherein R is arylalkyl or substituted arylalkyl.

4. A compound according to claim 2 wherein R is ethyl.

5. A compound according to claim 3 wherein R is arylalkyl.

6. A compound according to claim 3 wherein R is substituted arylalkyl.

7. A compound according to claim 5 wherein R is benzyl.

8. A compound according to claim 6 wherein R is methoxybenzyl.

9. The compound of claim 1 wherein the compound is selected from the group consisting of N-Hydroxy-N-(1-benzyl-2,3,4,5-tetrahydro-1H-1-benzazepin-7-yl)methylurea, N-hydroxy-N-[1-(3-methoxybenzyl)-2,3,4,5-tetrahydro-1H-1 -benzazepin-7-yl]methylurea, and N-Hydroxy-N-(1-ethyl-2,3,4,5 -tetrahydro-1H-1-benzazepin-7-yl)methylurea.

10. The compound of claim 1 wherein R is arylalkyl and wherein in said arylalkyl the aryl moiety is a phenyl group that optionally includes one or more substituents.

11. The compound of claim 1 wherein R is a methyl group.

12. A pharmaceutical composition for the treatment of allergy, inflammatory or cardiovascular conditions in a mammal comprising a therapeutically effective amount of a compound according to claim 1 or a pharmaceutically acceptable salt thereof together with a pharmaceutically acceptable carrier.

13. A method of inhibiting lipoxygenase in a mammal comprising administering to said mammal a lipoxygenase-inhibiting amount of a compound according to claim 1 or a pharmaceutically acceptable salt thereof.

14. A method of treating allergy or inflammatory or cardiovascular conditions in a mammal comprising administering to said mammal a lipoxygenase-inhibiting amount of a compound according to claim I or a pharmaceutically acceptable salt thereof.

* * * * *